(12) United States Patent
Asari

(10) Patent No.: US 8,153,614 B2
(45) Date of Patent: Apr. 10, 2012

(54) TREATMENT OF OSTEOARTHRITIS

(75) Inventor: Akira Asari, Tokyo (JP)

(73) Assignees: Glycoscience Laboratories, Inc., Tokyo (JP); Shiseido Co., Ltd., Tokyo (JP)

( * ) Notice: Subject to any disclaimer, the term of this patent is extended or adjusted under 35 U.S.C. 154(b) by 0 days.

(21) Appl. No.: 12/162,415

(22) PCT Filed: Dec. 5, 2006

(86) PCT No.: PCT/JP2006/324279
§ 371 (c)(1),
(2), (4) Date: Jul. 28, 2008

(87) PCT Pub. No.: WO2008/068854
PCT Pub. Date: Jun. 12, 2008

(65) Prior Publication Data
US 2010/0234322 A1 Sep. 16, 2010

(51) Int. Cl.
*A61K 31/702* (2006.01)
(52) U.S. Cl. .............................................. 514/61; 514/62
(58) Field of Classification Search .................. None
See application file for complete search history.

(56) References Cited

U.S. PATENT DOCUMENTS

| | | | |
|---|---|---|---|
| 5,646,129 | A | 7/1997 | Callegaro et al. |
| 5,840,546 | A | 11/1998 | Morikawa et al. |
| 5,939,403 | A | 8/1999 | Maruyama et al. |
| 6,013,641 | A | 1/2000 | Lussow et al. |
| 6,159,954 | A | 12/2000 | Maruyama et al. |
| 6,379,695 | B1 | 4/2002 | Donati et al. |
| 6,436,911 | B1 | 8/2002 | Asari et al. |
| 6,537,968 | B1 | 3/2003 | Lezdey et al. |
| 6,608,043 | B1 | 8/2003 | Serizawa et al. |
| 6,613,897 | B1 | 9/2003 | Yatsuka et al. |
| 6,894,034 | B1 | 5/2005 | Yatsuka et al. |
| 6,924,273 | B2 | 8/2005 | Pierce |
| 2004/0022847 | A1 | 2/2004 | Leneau |
| 2004/0071740 | A1 | 4/2004 | Petrigni et al. |
| 2004/0092479 | A1 | 5/2004 | Marcum |
| 2004/0097465 | A1 | 5/2004 | Asari et al. |
| 2004/0120925 | A1 | 6/2004 | Toda et al. |
| 2004/0171819 | A1 | 9/2004 | Viskov et al. |
| 2004/0265943 | A1 | 12/2004 | Viskov et al. |
| 2005/0090661 | A1 | 4/2005 | Asari et al. |
| 2005/0186679 | A1 | 8/2005 | Viskov et al. |
| 2006/0135439 | A1 | 6/2006 | Kato et al. |
| 2007/0123488 | A1 | 5/2007 | Balogh et al. |
| 2007/0134646 | A1 | 6/2007 | Asari et al. |
| 2007/0142323 | A1 | 6/2007 | Viskov et al. |
| 2008/0182983 | A1 | 7/2008 | Asari et al. |

FOREIGN PATENT DOCUMENTS

| | | |
|---|---|---|
| CA | 2414211 | 1/2003 |
| CA | 2 519 797 | 10/2004 |
| CA | 2519797 | 10/2004 |
| EP | 1034780 | 9/2000 |
| EP | 1166788 | 1/2002 |
| EP | 1300412 | 4/2003 |
| EP | 1407776 | 4/2004 |
| EP | 1611893 | 1/2006 |
| EP | 1634891 | 3/2006 |
| EP | 1767211 | 3/2007 |
| JP | 54-153291 | 12/1979 |
| JP | 1-272511 | 10/1989 |
| JP | 2-057182 | 2/1990 |
| JP | 60-16687 | 1/1994 |
| JP | 08-325161 | 12/1996 |
| JP | 97/11710 | 4/1997 |
| JP | 9-227386 | 9/1997 |
| JP | 11-310588 | 11/1999 |
| JP | 2000-191538 | 7/2000 |
| JP | 2001-089493 | 4/2001 |
| JP | 2001-97867 | 4/2001 |
| JP | 2002-029974 | 1/2002 |
| JP | 2003-171282 | 6/2003 |
| JP | 2004/050673 | 6/2004 |
| JP | 2004-238294 | 8/2004 |
| JP | 2004/104034 | 12/2004 |
| JP | 2005-089424 | 4/2005 |
| JP | 2005/049047 | 6/2005 |
| JP | 2005/067944 | 7/2005 |
| JP | 2005/090591 | 9/2005 |
| JP | 2006-500019 | 1/2006 |
| JP | 2006/040463 | 4/2006 |
| JP | 2006/077317 | 7/2006 |
| JP | 2006-517185 | 7/2006 |
| JP | 2006-335694 | 12/2006 |
| WO | 93/20827 | 10/1993 |
| WO | 96/016166 | 5/1996 |
| WO | 96/016973 | 6/1996 |
| WO | 02/04471 | 1/2002 |
| WO | 02/072144 | 9/2002 |
| WO | WO 2004/034980 | 4/2004 |
| WO | 2004/084912 | 10/2004 |

OTHER PUBLICATIONS

Asari, A. et al "Molecular weight-dependent effects of hyaluronate . . . " Arch. Histol. Cytol. (1998) vol. 61, No. 2, pp. 125-135.*
Ohno, S. et al "Induction of MMP-3 by hyaluronan oligosaccharides . . . " J. Dent. Res. (2005) vol. 84, No. 11, pp. 1005-1009.*
Knudson, W. et al "Hyaluronan oligosaccharides perturb cartilage matrix . . . " Arthritis Rheum. (2000) vol. 43, No. 5, pp. 1165-1174.*
Brandt et al. "Intraarticular Injection of Hyaluronan as Treatment for Knee Osteoarthritis", *Arthritis & Rheumatism* 43(6):1192-1203 (2000).
Maheu et al. "A Hyaluronan Preparation (500-730 KDA) in the Treatment of Osteoarthritis: A Review of Clinical Trials with Hyalgan®", *Int. J. Clinical Practice* 56(10):804-813 (2002).
Sezgin et al. "Does hyaluronan effect inflammatory cytokines in knew osteoarthritis?", *Ruematol. Int.* 25:264-269 (2005).
Wobig et al. "The Role of Elastoviscosity in the Efficacy of Viscosupplementation for Osteoarthritis of the Knee: A Comparison of Hylan G-F 20 and a Lower-Molecular-Weight Hyaluronan", *Clinical Therapeutics* 21(9):1549-1562 (1999).

(Continued)

*Primary Examiner* — Leigh Maier
(74) *Attorney, Agent, or Firm* — Myers Bigel Sibley & Sajovec, P.A.

(57) ABSTRACT

There is provided a therapeutic agent for treating osteoarthritis, which is a drug comprising hyaluronan as an active ingredient. The hyaluronan is preferably a tetrasaccharide including two units, with a single unit being -D-glucuronic acid-β-1,3-D-N-acetylglucosamine-β-1,4- (HA4).

3 Claims, No Drawings

OTHER PUBLICATIONS

Supplementary European Search Report corresponding to European Application No. 06834034.8 dated Feb. 9, 2010.
English language Abstract of JP 2006-335694.
Moreland, L.W., "Intra-articular Hyaluronan (hyaluronic acid) and Hylans for the Treatment of Osteoarthritis: Mechanisms of Action," Arthritis Res. Ther., 2003, vol. 5, No. 2, pp. 54-67.
Ohno et al, "Induction of MMP-3 by Hyaluronan Oligosaccharides in Temporomandibular Joint Chondrocytes," J. Dent. Res. 2005, vol. 84, No. 11, pp. 1005-1009.
Knudson et al., "Hyaluronan Oligosaccarides Perturb Cartilage Matrix Homeostasis and Induce Chondrocytic Chondrolysis," Arthritis Rheum, 2000, vol. 43, No. 5, pp. 1165-1174.
Xu H et al., "Effect of Hyaluronan Oligosachrides on the Expression of Heat Shock Protein 72," J. Biol. Chem., 2002 10; 277(19): 17308-14.
Takagaki et al., "Characterization of Hydrolysis and Transglycosylation by Testicular Hyaluronidase Using Ion-Spray Mass Spectrometry," Biochem., 33:6503-6507 (1994).
Kubo et al., "Depolymerization of hyaluronan by sonication," Glycoconjugate J., 10:435-439 (1993).
Tawada et al., "A. Larger-scale preparation, pufification, and characterization of hyaluronan oligosaccharides from 4-mers to 52-mers," Glycobiology, 2002; 12(7): 421-6.
Chang D G et al., "Quantitation and localization of cartilage degeneration following the induction of osteoarthritis in the rabbit knee," Osteoarthritis Cartilage, Sep. 1997 5(5): 357-72.
New Biochemistry Experiment Lecture (Shin-seikagaku jikken kouza) "Carbohydrate II: Proteoglycan and Glycosaminoglycan," pp. 244-249, 1991, Tokyo Kagaku-dojin Publishing Company, Inc., along with an English language partial translation thereof.
English language Abstract of JP 9-227386.
English language Abstract of JP 2003-171282.
English language Abstract of JP 1-272511.
English language Abstract of JP 2004-238294.
English language Abstract of JP 2001-97867.
English language Abstract of JP 11-310588.
English language Abstract of JP 2000-191538.
English language Abstract of JP 60-16687.
English language Abstract of JP 54-153291.
English language Abstract of JP 2-57182.
English language Abstract of JP 2001-089493.
English language Abstract of JP 8-325161.
English language Abstract of JP 2002-29974.
English language Abstract of JP 2005-89424.
A. Asari., "Novel Functions of Hyaluronan Oligosaccharides," Science of Hyaluronan Today, Editors: Vincent C. Hascal and M. Yanagishita, Glycoforum (2005).
M. Kim et al., "Rhodamine-123 Staining in Hematopoietic Stem Cells of Young Mice Indicates Mitochondrial Activation Rather than Dye Efflux," Blood, vol. 91, No. 11, pp. 4106-4117 (1998).
D. Aquino et al., "Multiple Sclerosis: Altered Expression of 70- and 27-kDa Heat Shock Proteins in Lesions and Myelin," Journal of Neuropathology and Experimental Neurology, vol. 56, No. 6, pp. 664-672 (1997).
M. Salvetti et al., "The Immune Response to Mycobacterial 70-kDa Heat Shock Proteins Frequently Involves Autoreactive T Cells and Is Quantitatively Disregulated in Multiple Sclerosis", Journal of Neuroimmunology, vol. 65, pp. 143-153 (1996).
H. Hoenig et al., "Disability Fingerprints: Patterns of Disability in Spinal Cord Injury and Multiple Sclerosis", Journal of Gerontology Medical Sciences, vol. 54A, No. 12, pp. M613-M620 (1999).
K. Kil et al., "T-Cell Responses to Myelin Basic Protein in Patients with Spinal Cord Injury and Multiple Sclerosis," Journal of Neuroimmunology, vol. 98, No. 2, pp. 201-207 (1999).
H. Cwiklinska et al., "Heat Shock Protein 70 Associations with Myelin Basic Protein and Proteolipid Protein in Multiple Sclerosis Brains," International Immunology, vol. 15, No. 2, pp. 241-249 (2003).
C. Cid et al., "Anti-Heat Shock Protein 90 β Antibodies are Detected in Patients with Multiple Sclerosis During Remission," Journal of Neuroimmunology, vol. 184, pp. 223-226 (2007).
C. Cid et al., "Antibodies Reactive to Heat Shock Protein 90 Induce Oligodendrocyte Precursor Cell Death in Culture. Implications for Demyelination in Multiple Sclerosis," FASEB Journal, vol. 18, No. 2, pp. 409-411 (2004).
M. Niino et al., "Heat Shock Protein 70 Gene Polymorphism in Japanese Patients with Multiple Sclerosis," Tissue Antigens, vol. 58, No. 2, pp. 93-96 (2001).
J. van Noort et al., "The Small Heat Shock Protein αB-Crystallin as Key Autoantigen in Multiple Sclerosis," Progress in Brain Research, vol. 117, Ch. 30, pp. 435-452 (1998).
J. van Noort et al., "The Small Heat-Shock Protein αB-Crystallin as Candidate Autoantigen, in Multiple Sclerosis," Nature, vol. 375, No. 6534, pp. 798-801 (1995).
K. Selmaj et al., "Expression of Heat Shock Protein-65 by Oligodendrocytes in Vivo and in Vitro: Implications for Multiple Sclerosis," Neurology, vol. 42, No. 4, pp. 795-800 (1992).
A. Vojdani et al., "Heat Shock Protein and Gliadin Peptide Promote Development of Peptidase Antibodies in Children with Autism and Patients with Autoimmune Disease," Clin. Diagn. Lab., Immunol., vol. 11, No. 3, pp. 515-524 (2004).
P. Wang et al., "The Role of Heat Shock Protein 70 and Its Autoantibody in Experimental Autoimmune Inner Ear Disease," Zhonghua Er Bi Yan Hou Ke Za Zhi, vol. 35, No. 1, pp. 10-13 (2000).
S.S. Gong et al., "Expression of Heat Shock Protein 70 in the Cochlea in Experimental Autoimmune Inner Ear Disease," Ann. Otol. Rhinol. Laryngol., vol. 111, No. 3, Part 1, pp. 275-280 (2002).
János et al., "Cink-Hyaluronát, A Richter Rt. Eredeti Organoterápiás Hatóanyaga," Acta Pharmaceutica Hungarica, vol. 72, pp. 15-24 (2002).
H. Xu et al., "The Keratan Sulfate Disaccharide Gal (6S03) β1,4-GlcNAc (6S03) Modulates Interleukin 12 Production by Macrophages in Murine Thy-1 Type Autoimmune Disease," The Journal of Biological Chemistry, vol. 280, No. 21, pp. 20879-20886 (2005).
H. Xu et al., "IL-12 Enhances Lymphoaccumulation by Suppressing Cell Death of T Cells in MRL-*lpr/lpr* Mice," Journal of Autoimmunity, vol. 16, pp. 87-95 (2001).
S. Basu et al., "Inflammatory Cytokine Concentrations are Elevated in Seminal Plasma of Men with Spinal Cord Injuries," Journal of Andrology, vol. 25, No. 2, pp. 250-254 (2004).
M. Kubota et al., "Characterization of Oligosaccharides of the Lactosamine Series Derived from Keratan Sulfates by Tandem Mass Spectrometry," Eur. J. Mass Spectrom., vol. 6, pp. 193-203 (2000).
D. Basso et al., "Graded Histological and Locomotor Outcomes after Spinal Cord Contusion Using the NYU Weigh-Drop Device versus Transection," Experimental Neurology, vol. 139, pp. 244-256 (1996).
D. Basso et al., "A Sensitive and Reliable Locomotor Rating Scale for Open Field Testing in Rats," Journal of Neurotrauma, vol. 12, No. 1, pp. 1-21 (1995).
Maytin et al., "Hyaluronan Participates in the Epidermal Response to Disruption of the Permeability Barrier in Vivo," American Journal of Pathology, 165(4):1331-1341 (2004).
MayoClinc.com, Peripheral Neuropathy, downloaded from www.mayoclinic.com/print/peripheral- neuropathy/DS00131/DSECTION=3 on Nov. 23, 2007.
WebMD.com, Brain & Nervous System Health Center, downloaded from webmd.com/brain/understanding-peripheral-neuropathy-basics?p.=3 on Nov. 23, 2007.
Pham et al., "Evaluation of the Symptomatic and Structural Efficacy of a New Hyaluronic Acid Compound, NRD101, in Comparison with Diacerein, and Placebo in a 1 Year randomized Controlled Study in Symptomatic Knee Osteoarthritis," Annals of the Rheumatic Diseases, vol. 63, pp. 1611-1617, 2004.
Ghosh et al., *Potential Mechanism of Action of Intra-articular Hyaluronan Therapy in Osteoarthritis: Are the Effects Molecular Weight Dependent?*, Seminars in Arthritis and Rheumatism, Aug. 2002, pp. 10-37, vol. 32, No. 1.
SIPO Office Action for corresponding Chinese Application No. 200680053571.5, Dispatch Date Apr. 23, 2010.
Response to SIPO Office Action (Dispatch Date Apr. 23, 2010) for corresponding Chinese Application No. 200680053571.5, Nov. 8, 2010.

* cited by examiner

TREATMENT OF OSTEOARTHRITIS

TECHNICAL FIELD

The present invention relates to a therapeutic agent for osteoarthritis comprising hyaluronan as an active ingredient.

BACKGROUND ART

Hyaluronan is a long-chain polysaccharide comprising disaccharide repeats of D-glucuronic acid and N-acetyl-D-glucosamine, and it is also known as an oligosaccharide. Hyaluronan is produced from an extract of a body tissue such as the cock's crest, umbilical cord, skin, or synovial fluid, by fermentation using bacteria of the genus *Streptococcus*, or the like. Since it has no toxicological or immunological effects, hyaluronan is utilized in drugs or cosmetics. For example, treatment of arthritis using an intraarticular injection of hyaluronan is well known. In the following description, HA4 denotes a tetrasaccharide hyaluronan.

It has been reported that HA4 has effects of preserving organs and treating/suppressing hepatopathy and stomach ulcers (Patent Document 1). Furthermore, HA4 is also known to have actions of enhancing the expression of stress proteins and inhibiting cell death (Non-patent Document 1).

Osteoarthritis is a joint disease associated with chronic arthritis, in which degeneration of components of the joint leads to destruction of the cartilage and proliferative change of the bone and cartilage. Furthermore, arthritis (synovitis) occurs secondarily due to the above-mentioned change. At an early stage, pain occurs after overuse of a joint and is relieved with rest. When the disease progresses, pain occurs even during light exercise or at rest, and night pain is often noted. Strong joint bending or extending or exercise makes a rapping noise, and accumulation of a synovial fluid may also occur due to the arthritic swollen joint.

On top of the degeneration of joint components (change with aging), genetic factors, aging, obesity, joint instability, repeated subluxation and luxation, excessive loads on joints due to labor, playing sports, and the like, and so forth are associated with progression of the disease.

Early treatments include administration of anti-inflammatory or analgesic drugs and application of a poultice or a tape containing an analgesic to relieve the pain. Exercise for strengthening the quadriceps femoris is effective for treatment of the knees. Exercise for abduction (lying and raising a leg) is effective for treatment of the hip joints. The use of a cane is also effective for osteoarthritis in the knee or hip joints since it reduces the load on the joints. Intraarticular injection of a joint protecting drug is also effective. Intraarticular steroid injection therapy should be performed with care since it may accelerate joint destruction if abused. When pain or degeneration is severe, surgical operations such as osteotomy and replacement with an artificial joint are indicated for treatment of the knee or hip joint.

[Patent Document 1] WO2002/004471
[Non-patent Document 1] Xu H, Ito T, Tawada A, Maeda H, Yamanokuchi H, Isahara K, Yoshida K, Uchiyama Y, Asari A. Effect of hyaluronan oligosaccharides on the expression of heat shock protein 72. J Biol Chem. 2002 10; 277(19): 17308-14.

DISCLOSURE OF THE INVENTION

An object of the present invention is to provide a therapeutic agent for treating osteoarthritis.

The therapeutic agent for treating osteoarthritis of the present invention, which achieves the above-mentioned object, includes hyaluronan as an active ingredient.

Since the drug of the present invention includes hyaluronan as an active ingredient, it has an advantage that it can be easily mass-produced at relatively low cost. Furthermore, since hyaluronan has virtually no toxicity or antigenicity and enhances therapeutic actions and disease preventing actions originally presented in organism, it is anticipated as a therapeutic agent with minimal adverse drug reactions. Thus, according to the present invention, a novel drug effective for treating osteoarthritis can be provided.

BEST MODE FOR CARRYING OUT THE INVENTION

Hereafter, the present invention will be explained in detail. In the following explanation, the therapeutic agent of the present invention will be simply referred to as a drug.

It is sufficient that hyaluronan contained in the drug of the present invention be a di- or higher saccharide basically containing at least one disaccharide unit being β-D-glucuronic acid at the 1st position and β-D-N-acetylglucosamine at the 3rd position linked to each other, and composed of basically 3-D-glucuronic acid and β-D-N-acetylglucosamine. Hyaluronan may also be a saccharide containing these elements bound to one or more disaccharide units or a derivative thereof. For example, hyaluronan having a hydrolysable protection group such as an acyl group and the like can also be used. This saccharide may be an unsaturated saccharide, and examples of the unsaturated saccharide include saccharides with a nonreducing end, glucuronic acid usually with unsaturation between carbons at the 4th and 5th positions, and so forth. Specifically, as hyaluronan used in the present invention, those extracted from natural products such as from animals, obtained by culturing microorganisms, chemically or enzymatically synthesized, and so forth can be used. For example, it can be obtained from body tissues such as the cock's crest, umbilical cord, skin, and synovial fluid by known extraction and purification methods. Furthermore, it can also be produced by fermentation using bacteria of the genus *Streptococcus*.

In the present invention, hyaluronan oligosaccharides are also encompassed in the scope of hyaluronan, and hyaluronans from those having a low molecular weight such as the above-mentioned disaccharide including one disaccharide unit and derivatives thereof, to high molecular weight hyaluronans having an average molecular weight of 4,000,000, can be used. Preferred examples thereof include hyaluronans having an average molecular weight of about 380 to 900,000, which are excellent in permeability in tissues and the like, and hyaluronans comprising about 2 to 20 saccharide units are more preferable.

Among hyaluronans, those having a low molecular weight are preferably produced, specifically, by methods for reducing the molecular weight of hyaluronan by known techniques such as enzymatic degradation, alkaline degradation, heat treatment, and ultrasonication (Biochem., 33 (1994) p 6503-6507), chemical or enzymatic synthesis method (Glycoconjugate J., (1993) pp. 435-439; WO93/20827), and the like. Examples of the enzymatic degradation technique include methods for producing hyaluronan oligosaccharides by acting enzymes that degrade hyaluronan such as hyaluronan degrading enzymes (hyaluronidase derived from the testicle, hyaluronidase derived from *Streptomyces*, hyaluronidase SD, etc.), chondroitinase AC, chondroitinase ACII, chondroitinase ACIII, and chondroitinase ABC on hyaluronan (refer to New Biochemistry Experiment Lecture "Carbohydrate II: Proteoglycan and glycosaminoglycan," pp. 244-248, 1991, Tokyo Kagaku-dojin Publishing Company, Inc.), and so forth.

Furthermore, examples of the alkaline degradation technique include a method for obtaining hyaluronan having a low molecular weight comprising the steps of adding a base such as about 1 N sodium hydroxide to a hyaluronan solution, heating the mixture for several hours to reduce the molecular weight, and adding an acid such as hydrochloric acid to neutralize the mixture, and so forth. The hyaluronan used in the present invention encompasses the form of a salt, and pharmacologically acceptable salts thereof can be used, if necessary, for formulation. For example, alkali metal salts such as sodium salts and potassium salts, alkaline earth metal salts such as calcium salts and magnesium salts, amine salts such as tri(n-butyl)amine salts, triethylamine salts, pyridine salts, and amino acid salts, and so forth.

The drug of the present invention is not particularly limited, and hyaluronan having a certain molecular weight can be used alone, or hyaluronans having various molecular weights may be used in combinations. The drug of the present invention comprises hyaluronan as an active ingredient, and osteoarthritis can be improved by administering an effective amount thereof to mammals including humans without adverse effect on an organism.

The drug of the present invention can be prepared using hyaluronan or a salt thereof as it is or with carriers, excipients, and other additives, if necessary, as a drug for oral or parenteral administration (interstitial administration such as intraarticular, intravenous, intramuscular, or subcutaneous administration (injection), enteral administration, percutaneous administration, etc.) in a freely selected dosage form, and is preferably administered to a patient by a freely selected method. It is particularly preferable to prepare the drug of the present invention as an oral formulation.

Examples of the oral formulation include solid formulations such as powders, granules, capsules, and tablets and liquid formulations such as syrups, elixirs, and emulsions. A powder can be obtained by mixing with, for example, an excipient such as lactose, starch, crystalline cellulose, calcium lactate, calcium hydrogen phosphate, magnesium aluminometasilicate, or anhydrous silicic acid. A granule can be obtained by further adding, for example, a binder such as sucrose, hydroxypropylcellulose, or polyvinylpyrrolidone, a binder such as carboxymethylcellulose or carboxymethylcellulose calcium, and a disintegrating agent such as carboxymethylcellulose or calcium carboxymethylcellulose, as required, in addition to the above-mentioned excipients and granulating the mixture by a wet or dry process. A tablet can be obtained by tableting the above-mentioned powder or granule as it is or adding a lubricant such as magnesium stearate or talc and tableting the mixture. Furthermore, the above-mentioned tablet or granule can be coated with an enteric vehicle such as hydroxypropylmethylcellulose phthalate, methyl methacrylate copolymers, or ethylcellulose, or Carunauba wax, hydrogenated oil, or the like to obtain an enteric or prolonged-action formulation. A hard capsule can be obtained by filling the above-mentioned powder or granule in a hard capsule. A soft capsule can be obtained by mixing hyaluronan or a salt thereof with glycerine, polyethylene glycol, sesame oil, olive oil, or the like and coating the mixture with a gelatin film. A syrup can be obtained by dissolving a sweetener such as sucrose, sorbitol, or glycerine and hyaluronan or a salt thereof in water. Furthermore, in addition to a sweetener and water, essential oil, ethanol, or the like can be added to obtain an elixir, or gum arabic, tragacanth, polysorbate 80, carboxymethylcellulose sodium, or the like can be added to obtain an emulsion or a suspension. Furthermore, flavoring agents, coloring materials, preservatives, and the like can be added to these liquid formulations as required.

Examples of the parenteral formulation include injection, intrarectal injection, pessary, transdermal topical agent, inhalant, aerosol, eye drops, and so forth. An injection formulation can be prepared by adding a pH modifier such as hydrochloric acid, sodium hydroxide, lactic acid, sodium lactate, monosodium hydrogen phosphate, or sodium dihydrogen phosphate; an isotonizing agent such as sodium chloride or glucose; and distilled water for injection, to hyaluronan or a salt thereof, sterilizing the mixture by filtration, and filling the mixture in an ampoule. Furthermore, an injection to be dissolved before use can be obtained by further adding mannitol, dextrin, cyclodextrin, gelatin, or the like and vacuum-freeze drying the mixture. Furthermore, an emulsion for injection can also be obtained by adding an emulsifier such as lecithin, polysorbate 80, or polyoxyethylene hydrogenated caster oil to hyaluronan or a salt thereof and emulsifying the mixture in water.

An intrarectal injection can be obtained by adding a vehicle for a suppository such as mono-, di-, or triglyceride of cacao fatty acid or polyethylene glycol to hyaluronan or a salt thereof, then dissolving with heating, pouring the mixture into a mold, and cooling it, or mixing hyaluronan or a salt thereof with polyethylene glycol, soybean oil, or the like and then coating the mixture with a gelatin film. A transdermal topical agent can be obtained by adding white Vaseline, beeswax, liquid paraffin, polyethylene glycol, or the like to hyaluronan or a salt thereof, heating the mixture, if necessary, and kneading the mixture. A tape can be obtained by kneading hyaluronan or a salt thereof with a tackifier such as rosin or an alkyl acrylate ester polymer and spreading the mixture on a non-woven fabric or the like. An inhalant can be obtained by dissolving or dispersing hyaluronan or a salt thereof in, for example, a propellant such as a pharmacologically acceptable inert gas and filling the mixture in a pressure-resistant container.

Administration Method

The method for administering the drug of the present invention comprising hyaluronan as an active ingredient is not particularly limited, and examples thereof include intravenous administration, oral administration, and intraarticular administration.

Dosage

The dosage is suitably determined depending on the disease to be treated, patient's age, health conditions, and body weight, and the like, and a common daily dose is 0.05 to 50 mg/kg which is taken once or divided into more than one dose.

Toxicity

The hyaluronan used in the present invention showed no or almost no cytotoxicity at doses at which biological activity as a medicament was observed.

EXAMPLES

The drug of the present invention will be explained more specifically with reference to the following examples. However, the technical scope of the present invention is not limited to these examples.

Example 1

In this example, HA4 was administered to C57BL/6 mice, which spontaneously develop osteoarthritis, to examine effects thereof.

Osteoarthritis Model Animal 20-week-old male C57BL/6 mice were purchased from Charles River Laboratories Japan, Inc., and animals which developed osteoarthritis were used. The animals were divided into the negative control (treated with physiological saline) group and the oral HA4 (100 mg/10 ml/kg) treated group.

Administration of Test Substance

In this example, 10 mg/ml HA4 was prepared. Specifically, HA4 was prepared by the method of Tawada et al. (Tawada A, Masa T, Oonuki Y, Watanabe A, Matsuzaki Y, Asari A. Large-scale preparation, purification, and characterization of hyaluronan oligosaccharides from 4-mers to 52-mers. Glycobiology. 2002; 12(7): 421-6.), and the concentration was adjusted with physiological saline. Furthermore, physiological saline was prepared as a control.

In this example, the test substance or physiological saline was orally given to mice which developed osteoarthritis using an oral sonde once daily for 2 weeks.

Macroscopic Examination

Osteoarthritis curing effects were determined macroscopically. Specifically, India ink was applied to the surface of the knee joint cartilage (shin bone and thigh bone) in all animals in each group and wiped with a gauze. The India ink remaining at the involved site was macroscopically examined using a blind and rated in 5 ranks (Table 1). For this evaluation method, refer to Chang D G, Iverson E P, Schinagl R M, Sonoda M, Amiel D, Coutts R D, Sah R L. Quantitation and localization of cartilage degeneration following the induction of osteoarthritis in the rabbit knee. Osteoarthritis Cartilage. 1997 September; 5(5): 357-72.

TABLE 1

| SCORE | PERCENTAGE OF REMAINING INDIA INK |
|---|---|
| 1 | 0-20% |
| 2 | 20-40% |
| 3 | 40-60% |

TABLE 1-continued

| SCORE | PERCENTAGE OF REMAINING INDIA INK |
|---|---|
| 4 | 60-80% |
| 5 | 80-100% |

Results

Results of macroscopic examination of osteoarthritis are shown in Table 2.

TABLE 2

| | SCORE FOR EACH ANIMAL | |
|---|---|---|
| PHYSIOLOGICAL SALINE GROUP | 5, 5, 4, 5, 5 | MEAN 4.8 |
| HA4 GROUP | 1, 2, 1, 2, 1 | MEAN 1.4 |

As a result of this example, therapeutic effects against osteoarthritis were confirmed in the HA4 treated group. This result demonstrated that a drug comprising hyaluronan as an active ingredient suppresses osteoarthritis.

The invention claimed is:

1. A method for treating osteoarthritis comprising a step of administering an effective amount of hyaluronan to a subject in need of such treatment, wherein the hyaluronan is a tetrasaccharide containing two units, with a single unit being -D-glucuronic acid-β-1,3-D-N-acetylglucosamine-β-1,4- and wherein the hyaluronan is orally administered.

2. The method according to claim 1, wherein the hyaluronan is orally administered daily.

3. The method according to claim 2, wherein the hyaluronan is orally administered daily in an amount between about 0.05 to about 50 mg/kg.

* * * * *